(12) United States Patent
Hanselmann et al.

(10) Patent No.: US 6,680,409 B2
(45) Date of Patent: Jan. 20, 2004

(54) PROCESS FOR THE PREPARATION OF ROBENIDINE AND SALTS THEREOF

(75) Inventors: Paul Hanselmann, Brig-Glis (CH); Stefan Hildbrand, Riehen (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/900,409

(22) Filed: Jul. 6, 2001

(65) Prior Publication Data

US 2002/0123649 A1 Sep. 5, 2002

Related U.S. Application Data

(63) Continuation of application No. PCT/EP00/00050, filed on Jan. 5, 2000.
(60) Provisional application No. 60/146,107, filed on Jul. 29, 1999.

(30) Foreign Application Priority Data

Jan. 6, 1999 (EP) .............................................. 99100097

(51) Int. Cl.[7] ........................................... C07C 277/00
(52) U.S. Cl. ...................................................... 564/232
(58) Field of Search ......................................... 564/232

(56) References Cited

U.S. PATENT DOCUMENTS

| | | | | |
|---|---|---|---|---|
| 3,901,944 A | * | 8/1975 | Tomcufcik | |
| 3,992,446 A | * | 11/1976 | Tomcufcik | |
| 4,575,560 A | | 3/1986 | Addor et al. | |

FOREIGN PATENT DOCUMENTS

| | | | |
|---|---|---|---|
| DE | 1933112 | * | 6/1969 |
| GB | 1256723 | | 12/1971 |
| WO | 9218444 | | 10/1992 |
| WO | 9745529 | | 12/1997 |

OTHER PUBLICATIONS

Shestakov et al. "Synthesis of Khimkoktsid—1.3–bis–(p–chlorobenzylideneamino) guanidine, labeled with the radionuclides $^{14}C$ and $^{3}H$, and its pharmacokinetics," *Khim.–Farm. Zh.* 1981, 15(1), 23–28.
Shestakov et al. "Synthesis of Khimkoktsid—1, 3–bis–(p–chlorobenzylideneamino) guanidine, labeled with the radionuclides $^{14}C$ and $^{3}H$, and its pharmacokinetics," *Pharm. Chem. J.* 1981, 15(1), 4–9.

Shestakov et al., "Synthesis of khimkoktsid, 1, 3–bis (p–chlorobenzylidenamino)guanidine, labeled with the radionuclides carbon–14 and hydrogen–3, and its pharmacokinetics", p. 6765, *CHem. Abstracts*, vol. 95, No. 1, Jul. 6, 1981, Abstract No. 6756j.

* cited by examiner

*Primary Examiner*—Johann Richter
*Assistant Examiner*—Paul A. Zucker
(74) *Attorney, Agent, or Firm*—Baker Botts L.L.P.

(57) ABSTRACT

The invention relates to a novel method for producing robenidine and salts thereof of the general formula

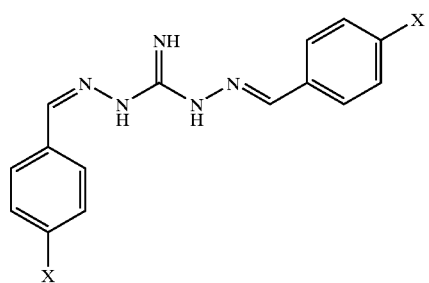

I wherein X denotes a halogen atom. The method uses hydrazine hydrate and a cyano compound YCN as the starting materials, which are first reacted to projuce a diaminoguanidine of the general formula

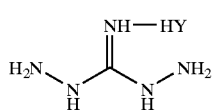

III

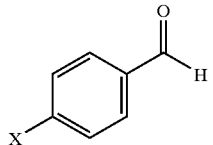

IV wherein Y denotes a halogen atom or tosyl. This diaminoguanidine is then converted directly, without isolation, by reacting with a p-halobenzaldehyde of the general formula IV to produce the robenidine and salts thereof of general formula I.

16 Claims, No Drawings

PROCESS FOR THE PREPARATION OF ROBENIDINE AND SALTS THEREOF

The present application is a continuation of PCT Application No. PCT/EP00/00050 filed Jan. 5, 2000, published in German as International Publication No. WO 00/40549 on Jul. 13, 2000. Priority from EPO Application No. 99100097.7, filed Jan. 6, 1999 and U.S. Provisional Application Ser. No. 60/146,107, filed Jul. 29, 1999 is claimed.

BACKGROUND OF THE INVENTION

The invention relates to a novel process for the preparation of robenidine and salts thereof of the general formula

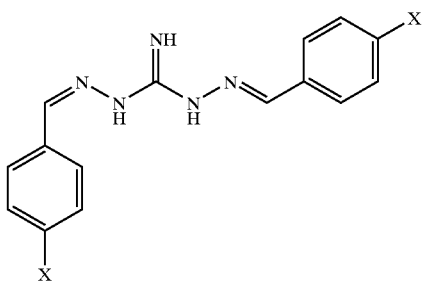

in which X denotes a halogen atom, utilizing hydrazine hydrate and a cyanogen halide are starting materials.

In Chemical Abstract No. 6745j to Shestakov et al., a process for preparing robenidine containing $^{14}C$ and $^{3}H$ isotopes is disclosed. Another reference disclosing robenidine compounds and their derivatives is U.S. Pat. No. 4,575,560 to Addor et al. The Addor reference discloses the use of such compounds as antiprotozoal agents, specifically anticoccidial agents, as well as insecticidal agents that exhibit antifeeding activity when applied to plants. However, in both of the above references, the intermediate diaminoguanidine salt that is formed must be separated off prior to further processing. Thus, these references disclose processes in which robenidine is prepared from a diaminoguanidine salt which has already been isolated.

As disclosed in a German patent reference (DE 19 33 112 A1 to American Cyanamid Co.), robenidine, 1, 3-bis [(4-chlorobenzylidene) amino] guanidine, and robenidine derivatives may be employed for controlling coccidiosis infections in poultry, and such compounds may act as active antimalaria agents for homeotherms. This reference discloses a process for preparing robenidine wherein dichlorobenzaldehyde or p-chlorobenzaldehyde is reacted with a diaminoguanidine salt, for example 1, 3-diaminoguanadine nitrate, in ethanol to give the desired product. A disadvantage of this process is the fact that the product is obtained in only moderate yield.

SUMMARY OF THE INVENTION

It was an object of the present invention to provide a "one-pot" process for the preparation of robenidine wherein the desired product is obtained in excellent yield and purity.

It was a further object of the present invention to convert the diaminoguanidine salt produced in the first step of the process directly into the end product without isolation and purification of the intermediate.

Still another object of the present invention involves providing a process for producing robenidine and salts thereof in both a simple and economical manner.

These objects are achieved through a process for preparing robenidine and salts thereof, wherein the robenidine and its salts have the general formula

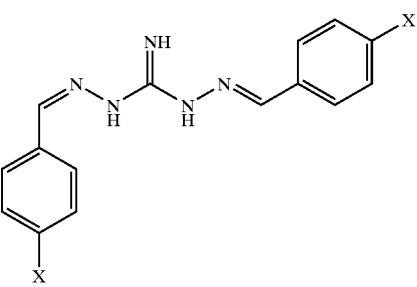

and wherein X is a halogen atom. In this process, hydrazine hydrate is reacted with a cyano compound in a $C_{1-4}$-alcohol or a $C_{1-4}$-alcohol/water mixture as the solvent, to produce a diaminoguanidine. Subsequently, the diaminoguanidine is converted directly, without isolation, by reacting with a p-halobenzaldehyde in a $C_{1-4}$-alcohol/water mixture as the solvent, to produce the robenidine and salts thereof of general formula I.

These and other objects of the present invention will be more fully understood from the following description of the invention.

DETAILED DESCRIPTION OF THE INVENTION

According to the invention, the process is carried out such that in a first step, hydrazine hydrate is reacted with a cyano compound of the general formula <p align="center">Y—CN      II</p> in which Y denotes a halogen atom or tosyl. This reaction takes place in a $C_{1-4}$-alcohol or a $C_{1-4}$-alcohol/water mixture as solvent or in an aprotic polar organic solvent and produces a diaminoguanidine of the general formula

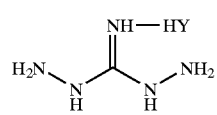

III

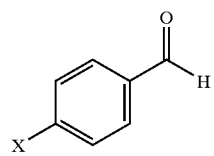

IV in which Y has the meaning stated above. This diaminoguanidine is converted directly, without isolation, by reacting in a second step with a p-halobenzaldehyde of the general formula

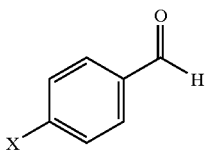

(in which X denotes a halogen atom), in a $C_{1-4}$-alcohol or a $C_{1-4}$-alcohol/water mixture as solvent or in a mixture of an aprotic organic solvent and water, into the end product of the formula

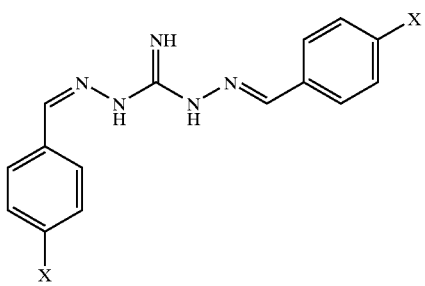

in which X denotes a halogen atom. The end product may also be a salt of the end product shown above in Formula I.

Y may be a halogen, for instance, fluorine, chlorine, bromine or iodine, or Y may be tosyl. In certain preferred embodiments, Y denotes chlorine, bromine or tosyl. Furthermore, the cyano compounds used in the first step may be cyanogen chloride, cyanogen bromide, or tosyl cyanide. In certain preferred embodiments, the cyano compound employed is cyanogen chloride.

The $C_{1-4}$-alcohols used as solvents may be methanol, ethanol, propanol, isopropanol, butanol, isobutanol or tert-butanol. In certain preferred embodiments, isopropanol is used as the solvent.

The aprotic polar solvents used may be ethers, glycol ethers or organic nitrogen compounds. The ethers used may be, for example, dioxane or tetrahydrofuran, and the glycol ethers used may be, for example, mono-, di-, tri- or poly-ethylene glycol ether. The organic nitrogen compounds used may be, for example, acetonitrile, propionitrile or dimethylformamide.

In certain embodiments, it is preferable to carry out the first step of the process in a $C_{1-4}$-alcohol/water mixture. The mixing ratio (% by weight) for such an alcohol/water mixture may range from 1:1 to 15:1. In certain preferred embodiments, this mixing ratio ranges from 4:1 to 10:1.

The starting materials, the hydrazine hydrate and the cyano compounds, such as cyanogen chloride, are commercially available compounds.

The reaction of the first step may be carried out at a temperature of from −30° to 50° C., while certain preferred embodiments are carried out at a temperature of from −10° to 30° C. Other preferred embodiments may be carried out at a temperature of from 0° to 20° C.

X is a halogen atom such as fluorine, chlorine, bromine, or iodine. In certain preferred embodiments, X denotes chlorine or bromine, and in still other preferred embodiments, X is chlorine.

Accordingly, the p-halobenzaldehydes used may be, for example, p-chlorobenzaldehyde or p-bromobenzaldehyde. In certain preferred embodiments, p-chlorobenzaldehyde is used.

The process in the second step may be carried out at a temperature of from 50° to 90° C., while certain preferred embodiments are carried out at a temperature of from 65° to 85° C.

The second step may utilize the same $C_{1-4}$-alcohols and the same aprotic polar organic solvents as in the first step. However, as described above, the second step can also be carried out in a mixture of water and an aprotic polar solvent. The ratio of water/aprotic polar organic solvent (% by weight) is advantageously 10:1 to 1:1, preferably 2:1 to 1:1.

In a particularly preferred embodiment, the solvent used in the first step is diluted with water prior to the second step, especially if no aqueous solvent was used in the first step.

The second step of the reaction or process may be carried out at a pH below 3, while certain preferred embodiments may be carried out at a pH of from 0.5 to 1.5. The pH may be established by the addition of a mineral acid, for example, hydrochloric acid, nitric acid, or sulfuric acid.

After a customary reaction time of from 0.5 to 3 h, the robenidine or a derivative thereof may be obtained, by customary work-up methods, as a salt in excellent yield and purity. Salts of robenidine or of robenidine derivatives which may be prepared according to the invention include, for example, the hydrohalide salts, such as the hydrochloride or hydrobromide salts.

EXAMPLES

Example 1

Preparation of Robenidine Hydrochloride

Over a period of 40 minutes, 16.0 g (0.26 mol) of cyanogen chloride were introduced into a solution cooled to 0° C. containing 25.0 g (0.50 mol) of hydrazine hydrate and 200 mL of isopropanol such that the temperature did not exceed 12° C. The pH was then measured to be 9.9.1.0 gram portions of cyanogen chloride were then added until the pH was less than 4. In this particular example, the pH was lowered to 3.8 after the addition of three 1.0 gram portions of cyanogen chloride.

After a 20-minute period of stirring at 10° C., 130 mL of $H_2O$ were added, and the pH was adjusted to 1.0 by the drop-wise addition of 10.63 g of concentrated hydrochloric acid. The reaction mixture was subsequently heated to 70° C. When the internal temperature of the reaction mixture was 61° C., metered addition of 61.55 g (0.44 mol) of molten p-chlorobenzaldehyde (which has a melting point of 46° C.) was initiated. This drop-wise addition was completed after 20 minutes.

A white suspension was obtained which was heated to 80° C. over a period of 10 minutes and then stirred at 80° C. for another 45 minutes. The reaction mixture was subsequently cooled to 15° C. and centrifuged. The residue was washed with 50 mL portions of $H_2O$ until the pH of the wash water was greater than 3. The pH reached a level of greater than 3 after the addition of six 50 mL portions of $H_2O$. Further washing with isopropanol (two 50 mL portions) and ethyl acetate (two 50 mL portions) yielded 81.70 g of moist robenidine hydrochloride, which was dried in a drying cabinet at 90° C./20 mbar for 48 hours. The end product obtained included 75.70 g (81.7%) of robenidine hydrochloride as a white solid, having a content of 99.1%, where this purity value was determined by HPLC analysis.

In another reaction carried out analogously to the above-described reaction, an exact amount of cyanogen chloride (0.26 mL) was added without regard to whether the resulting pH was below 4. This produced robenidine hydrocholoride with the same yield.

Example 2

Over a period of 3 hours, 15.5 g (0.25 mol) of cyanogen chloride were introduced into a solution (which had been cooled to 0° C.) of 25.0 g (0.50 mol) hydrazine hydrate in 215 mL of an isopropanol and water mixture, mixed at a mixing ratio of 88:12 (% by weight). The cyanogen chloride was introduced such that the temperature of the solution did not exceed 20° C. Following an additional reaction time of 10 minutes at 10° C., 155 mL of H₂O were added, and the pH was adjusted to 1.0 using 16.2 g of concentrated hydrochloric acid. The solution, which was now clear, was subsequently heated to 70° C., and 61.5 g (0.44 mol) of molten p-chlorobenzaldehyde were added drop-wise. The suspension was then heated to 80° C. and stirred at this temperature for 45 minutes. The reaction mixture was cooled to 15° C. and centrifuged. The residue was washed with six 50 mL portions of H₂O and two 50 mL portions of isopropanol and then dried in a drying cabinet at 90° C./20 mbar for 15 hours. This reaction produced 77.5 g (84%, based on hydrazine hydrate) of robenidine hydrochloride as a white solid, and the purity of the product was determined to be 99.6% by HPLC analysis.

Example 3 to 10

Examples 3 to 10 were carried out under the same conditions as in Examples 1 or 2; however, the solvent was varied. The results of Examples 1 to 10 are summarized in Table 1.

TABLE 1

| Example | Solvent for Step 1 | Solvent for Step 2 | Yield [%] | Purity [%] |
|---|---|---|---|---|
| 1 | isopropanol (i-PrOH) | i-PrOH/H₂O mixture | 82 | 99.1 |
| 2 | i-PrOH/H₂O 88:12 | i-PrOH/H₂O mixture | 84 | 99.6 |
| 3 | methanol (MeOH) | MeOH/H₂O mixture | 73 | 89.0 |
| 4 | ethanol (EtOH)/H₂O 96:4 | EtOH/H₂O mixture | 77 | 92.7 |
| 5 | n-butanol | n-BuOH/H₂O mixture | 76 | 92.2 |
| 6 | 2-butanol | 2-butanol/H₂O mixture | 69 | 89.6 |
| 7 | tetrahydrofuran (THF) | THF/H₂O mixture | 75 | 83.4 |
| 8 | acetonitrile (MeCN) | MeCN/H₂O mixture | 75 | 88.5 |
| 9 | MeOH | MeOH/i-PrOH/H₂O 4:3:1 | 76 | 83.2 |
| 10 | MeOH | MeOH | 64 | 85.1 |

In the above Examples, the solvent for step 2 is understood to be the solvent mixture which is obtained by the addition of water (except for Example 10, where the dilution was carried out using methanol) after the metered addition of cyanogen chloride, but prior to the metered addition of chlorobenzaldehyde. Generally, the amount of water added for step 2 was such that the mixing ratio of water to alcohol (or water to other component, such as an aprotic organic solvent) ranged from 3:2 to 1:1 (% by weight). Furthermore, all purity values were determined by HPLC analysis.

What is claimed is:

1. Process for preparing robenidine and salts thereof, said robenidine and its salts having the general formula

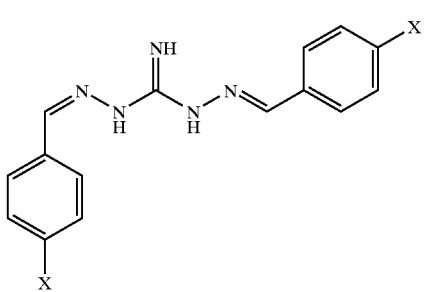

in which X is a halogen atom, said process comprising reacting hydrazine hydrate with a cyano compound of the general formula

in which Y is a halogen atom or tosyl, in a $C_{1-4}$-alcohol or a $C_{1-4}$-alcohol/water mixture as solvent or in an aprotic polar organic solvent, to produce a diaminoguanidine of the general formula

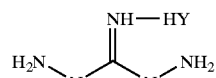

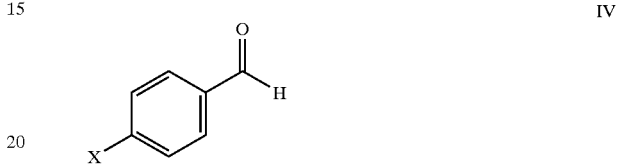

in which Y is a halogen atom or tosyl,
  said diaminoguanidine then being converted directly, without isolation, by reacting with a p-halobenzaldehyde of the general formula

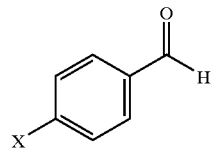

wherein X is a halogen atom, in a $C_{1-4}$-alcohol/water mixture as solvent or in a mixture of water and an aprotic organic solvent, into the robenidine and salts thereof of general formula I.

2. The process according to claim 1, wherein the reaction of the hydrazine hydrate and the cyano compound is carried out at a temperature of from −30° to 50° C.

3. The process according to claim 1, wherein the cyano compound is cyanogen chloride.

4. The process according to claim 3, wherein the reaction is carried out at a temperature of from −30° to 50° C.

5. The process according to claim 1, wherein the p-halobenzaldehyde is p-chlorobenzaldehyde.

6. The process according to claim 1, wherein the reaction of the diaminoguanidine with a p-halobenzaldehyde is carried out at a temperature of from 50° to 90° C.

7. Process for preparing the hydrochloride of robenidine having the formula

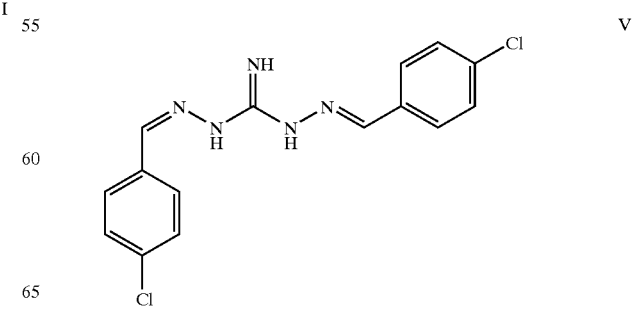

said process comprising reacting hydrazine hydrate with cyanogen chloride in a mixture comprising isopropanol and water at a mixing ratio of from 1:1 to 15:1 (% by weight) as the solvent, at a temperature of from −10° to 30° C., to produce a diaminoguanidine, said diaminoguanidine then being converted directly, without isolation, by reacting with p-chlorobenzaldehyde, in a mixture comprising isopropanol and water at a mixing ratio of from 1:1 to 15:1 (% by weight) as the solvent, at a temperature of from 50° to 90° C., to produce the hydrochloride of robenidine having the formula V.

8. Process for preparing the hydrochloride of robenidine having the formula

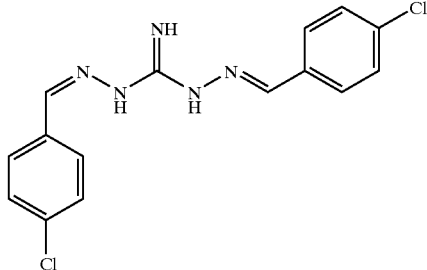

V said process comprising reacting hydrazine hydrate with cyanogen chloride in isopropanol as the solvent, at a temperature of from −10° to 30° C., to produce a diaminoguanidine, said diaminoguanidine then being converted directly, without isolation, by reacting with p-chlorobenzaldehyde, in a mixture comprising isopropanol and water at a mixing ratio of from 1:1 to 15:1 (% by weight) as the solvent, at a temperature of from 50° to 90° C., to produce the hydrochloride of robenidine having the formula V.

9. Process for preparing the hydrochloride of robenidine having the formula

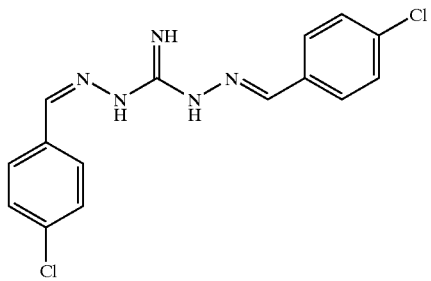

V said process comprising reacting hydrazine hydrate with cyanogen chloride in methanol as the solvent, at a temperature of from −10° to 30° C., to produce a diaminoguanidine, said diaminoguanidine then being converted directly, without isolation, by reacting with p-chlorobenzaldehyde, in a mixture comprising methanol and water at a mixing ratio of from 1:1 to 15:1 (% by weight) as the solvent, at a temperature of from 50° to 90° C., to produce the hydrochloride of robenidine having the formula V.

10. Process for preparing the hydrochloride of robenidine having the formula

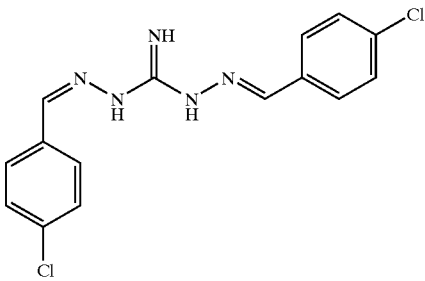

V said process comprising reacting hydrazine hydrate with cyanogen chloride in a mixture comprising ethanol and water at a mixing ratio of from 1:1 to 25:1 (% by weight) as the solvent, at a temperature of from −10° to 30° C., to produce a diaminoguanidine, said diaminoguanidine then being converted directly, without isolation, by reacting with p-chlorobenzaldehyde, in a mixture comprising ethanol and water at a mixing ratio of from 1:1 to 25:1 (% by weight) as the solvent, at a temperature of from 50° to 90° C., to produce the hydrochloride of robenidine having the formula V.

11. Process for preparing the hydrochloride of robenidine having the formula

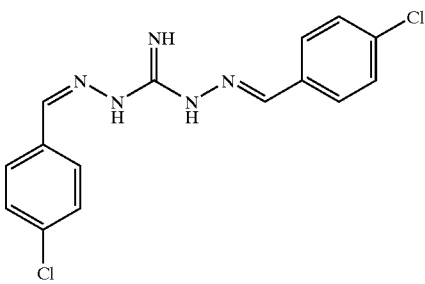

V said process comprising reacting hydrazine hydrate with cyanogen chloride in n-butanol as the solvent, at a temperature of from −10° to 30° C., to produce a diaminoguanidine, said diaminoguanidine then being converted directly, without isolation, by reacting with p-chlorobenzaldehyde, in a mixture comprising n-butanol and water at a mixing ratio of from 1:1 to 15:1 (% by weight) as the solvent, at a temperature of from 50° to 90° C., to produce the hydrochloride of robenidine having the formula V.

12. Process for preparing the hydrochloride of robenidine having the formula

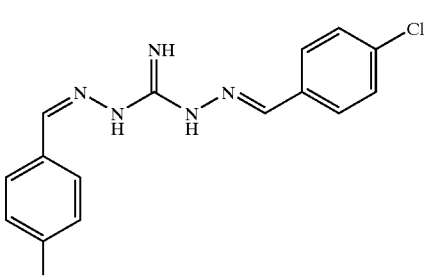

V said process comprising reacting hydrazine hydrate with cyanogen chloride in 2-butanol as the solvent, at a temperature of from −10° to 30° C., to produce a diaminoguanidine, said diaminoguanidine then being converted directly, without isolation, by reacting with p-chlorobenzaldehyde, in a mixture comprising 2-butanol and water at a mixing ratio of from 1:1 to 15:1 (% by weight) as the solvent, at a temperature of from 50° to 90° C., to produce the hydrochloride of robenidine having the formula V.

13. Process for preparing the hydrochloride of robenidine having the formula

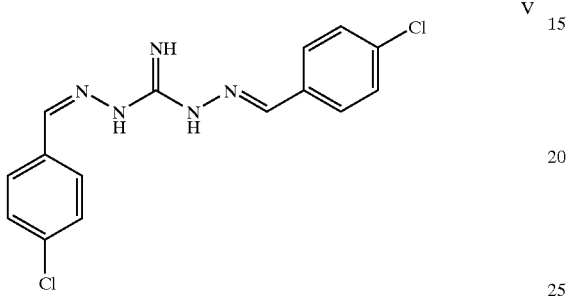

V said process comprising reacting hydrazine hydrate with cyanogen chloride in tetrahydrofuran as the solvent, at a temperature of from −10° to 30° C., to produce a diaminoguanidine, said diaminoguanidine then being converted directly, without isolation, by reacting with p-chlorobenzaldehyde, in a mixture comprising tetrahydrofuran and water at a mixing ratio of from 1:1 to 15:1 (% by weight) as the solvent, at a temperature of from 50° to 90° C., to produce the hydrochloride of robenidine having the formula V.

14. Process for preparing the hydrochloride of robenidine having the formula

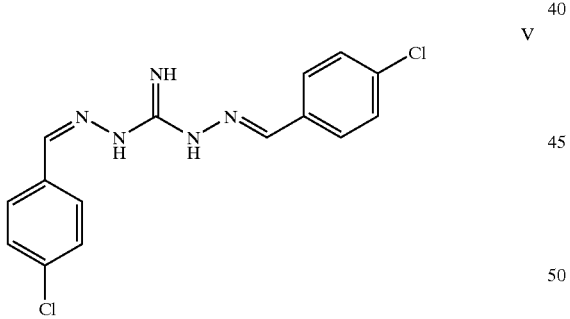

V said process comprising reacting hydrazine hydrate with cyanogen chloride in acetonitrile as the solvent, at a temperature of from −10° to 30° C., to produce a diaminoguanidine, said diaminoguanidine then being converted directly, without isolation, by reacting with p-chlorobenzaldehyde, in a mixture comprising acetonitrile and water at a mixing ratio of from 1:1 to 15:1 (% by weight) as the solvent, at a temperature of from 50° to 90° C., to produce the hydrochloride of robenidine having the formula V.

15. Process for preparing the hydrochloride of robenidine having the formula

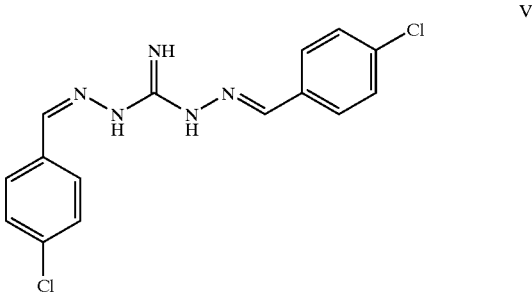

V said process comprising reacting hydrazine hydrate with cyanogen chloride in methanol as the solvent, at a temperature of from −10° to 30° C., to produce a diaminoguanidine, said diaminoguanidine then being converted directly, without isolation, by reacting with p-chlorobenzaldehyde, in a mixture comprising methanol, isopropanol, and water at a mixing ratio of 4:3:1 (% by weight) as the solvent, at a temperature of from 50° to 90° C., to produce the hydrochloride of robenidine having the formula V.

16. Process for preparing the hydrochloride of robenidine having the formula

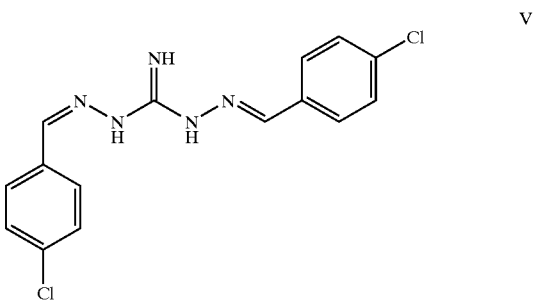

V said process comprising reacting hydrazine hydrate with cyanogen chloride in methanol as the solvent, at a temperature of from −10° to 30° C., to produce a diaminoguanidine, said diaminoguanidine then being converted directly, without isolation, by reacting with p-chlorobenzaldehyde, in methanol as the solvent, at a temperature of from 50° to 90° C., to produce the hydrochloride of robenidine having the formula V.

* * * * *

UNITED STATES PATENT AND TRADEMARK OFFICE
CERTIFICATE OF CORRECTION

PATENT NO. : 6,680,409 B2
DATED : January 20, 2004
INVENTOR(S) : Hanselmann et al.

It is certified that error appears in the above-identified patent and that said Letters Patent is hereby corrected as shown below:

Title page,
Item [56], References Cited, OTHER PUBLICATIONS,
"Shestakov et al." reference, (third occurrence) "(p-chlorobenzylidenamino)" should read -- (p-chlorobenzylideneamino) --; and "*CHem.*" should read -- *Chem.* --
Item [57], ABSTRACT,
Line 5, "projuce" should read -- produce --

Column 2,
Lines 56-61, delete Formula IV

Column 4,
Line 27, "9.9.1.0" should read -- 9.9. 1.0 --
Line 57, "hydrocholoride" should read -- hydrochloride --

Column 6,
Lines 15-20, delete Formula IV

Signed and Sealed this

Twenty-third Day of November, 2004

JON W. DUDAS
*Director of the United States Patent and Trademark Office*